United States Patent
Ye et al.

(10) Patent No.: US 11,072,571 B2
(45) Date of Patent: *Jul. 27, 2021

(54) FLUIDIZED BED REACTOR AND METHOD FOR PRODUCING PARA-XYLENE AND CO-PRODUCING LIGHT OLEFINS FROM BENZENE AND METHANOL AND/OR DIMETHYL ETHER

(71) Applicant: DALIAN INSTITUTE OF CHEMICAL PHYSICS, CHINESE ACADEMY OF SCIENCES, Dalian (CN)

(72) Inventors: Mao Ye, Dalian (CN); Tao Zhang, Dalian (CN); Jinling Zhang, Dalian (CN); Zhongmin Liu, Dalian (CN); Jinming Jia, Dalian (CN); Hailong Tang, Dalian (CN); Changqing He, Dalian (CN); Xiangao Wang, Dalian (CN); Cheng Zhang, Dalian (CN); Hua Li, Dalian (CN); Yinfeng Zhao, Dalian (CN); Chenggong Li, Dalian (CN)

(73) Assignee: DALIAN INSTITUTE OF CHEMICAL PHYSICS, CHINESE ACADEMY OF SCIENCES, Dalian (CN)

( * ) Notice: Subject to any disclaimer, the term of this patent is extended or adjusted under 35 U.S.C. 154(b) by 0 days.

This patent is subject to a terminal disclaimer.

(21) Appl. No.: 16/608,444

(22) PCT Filed: Nov. 24, 2017

(86) PCT No.: PCT/CN2017/112812
§ 371 (c)(1),
(2) Date: Oct. 25, 2019

(87) PCT Pub. No.: WO2018/196362
PCT Pub. Date: Nov. 1, 2018

(65) Prior Publication Data
US 2020/0199040 A1    Jun. 25, 2020

(30) Foreign Application Priority Data
Apr. 27, 2017    (CN) .......................... 201710288532.3

(51) Int. Cl.
*B01J 8/24*      (2006.01)
*B01J 4/00*      (2006.01)
(Continued)

(52) U.S. Cl.
CPC ............... *C07C 2/864* (2013.01); *B01J 4/004* (2013.01); *B01J 8/1827* (2013.01); *B01J 8/1863* (2013.01);
(Continued)

(58) Field of Classification Search
None
See application file for complete search history.

(56) References Cited

U.S. PATENT DOCUMENTS 2,456,035 A * 12/1948 Wobker ................. C10G 11/18
208/155
2,539,415 A *  1/1951 Garbo ................... B01J 8/1818
518/712
(Continued)

FOREIGN PATENT DOCUMENTS

CA    2297428 A1 *  7/2000  ............ B01J 8/1872
CN    1208433 C        6/2005
(Continued)

OTHER PUBLICATIONS

CN101940898_English Translation (Year: 2011).*
(Continued)

*Primary Examiner* — Jennifer A Leung
(74) *Attorney, Agent, or Firm* — Maier & Maier, PLLC

(57) ABSTRACT

A fluidized bed reactor for producing para-xylene and co-producing light olefins from benzene and methanol and/or (Continued)

dimethyl ether, including a first distributor and a second distributor. The first distributor is located at the bottom of the fluidized bed, and the second distributor is located at the downstream of the first distributor along a gas flow direction. Also, a method for producing para-xylene and co-producing light olefins, including the following steps: a material stream A enters a reaction zone of the fluidized bed reactor from the first gas distributor; a material stream B enters the reaction zone of the fluidized bed reactor from the second gas distributor; a reactant contacts a catalyst in the reaction zone to generate a gas phase stream comprising para-xylene and light olefins.

14 Claims, 3 Drawing Sheets

(51) Int. Cl.
    *C07C 2/86*       (2006.01)
    *C07C 15/08*     (2006.01)
    *B01J 8/18*       (2006.01)
    *C07C 1/24*       (2006.01)
    *C07C 2/88*       (2006.01)

(52) U.S. Cl.
    CPC .................. *B01J 8/24* (2013.01); *C07C 1/24* (2013.01); *C07C 2/865* (2013.01); *C07C 2/88* (2013.01); *C07C 15/08* (2013.01); *B01J 2208/00752* (2013.01); *B01J 2208/00911* (2013.01); *C07C 2529/40* (2013.01)

(56) References Cited

U.S. PATENT DOCUMENTS

| | | | |
|---|---|---|---|
| 2,768,127 A * | 10/1956 | Kimberlin, Jr. .......... | C10G 9/32 208/50 |
| 2,893,849 A | 7/1959 | Krebs | |
| 3,298,793 A * | 1/1967 | Mallison .................... | B01J 8/44 422/143 |
| 4,051,069 A | 9/1977 | Bunn, Jr. et al. | |
| 4,070,393 A | 1/1978 | Angstadt et al. | |
| 4,337,120 A | 6/1982 | Spars et al. | |
| 4,456,504 A | 6/1984 | Spars et al. | |
| 4,691,031 A | 9/1987 | Suciu et al. | |
| 5,965,765 A | 10/1999 | Kurihara et al. | |
| 6,894,183 B2 | 5/2005 | Choudhary et al. | |
| 9,095,831 B2 | 8/2015 | Han et al. | |
| 9,346,916 B2 * | 5/2016 | Wang ..................... | B01J 8/1818 |
| 2002/0182123 A1 | 12/2002 | Ramachandran et al. | |
| 2012/0217440 A1 * | 8/2012 | Tetzlaff .................... | C10J 3/503 252/373 |
| 2020/0188869 A1 * | 6/2020 | Zhang ..................... | B01J 8/005 |

FOREIGN PATENT DOCUMENTS

| | | | | |
|---|---|---|---|---|
| CN | 101239870 A | | 8/2008 | |
| CN | 101279873 A | | 10/2008 | |
| CN | 201384946 Y | | 1/2010 | |
| CN | 101940898 | * | 1/2011 | ................ B01J 8/24 |
| CN | 101940898 A | | 1/2011 | |
| CN | 101954264 A | | 1/2011 | |
| CN | 101723702 B | | 2/2012 | |
| CN | 102464557 A | | 5/2012 | |
| CN | 102875318 A | | 1/2013 | |
| CN | 203379868 U | | 1/2014 | |
| CN | 104177210 A | | 12/2014 | |
| CN | 104549073 A | | 4/2015 | |
| CN | 204447967 U | | 7/2015 | |
| CN | 102372585 B | | 12/2015 | |
| CN | 106588527 A | | 4/2017 | |
| CN | 108794294 A | | 11/2018 | |
| EP | 1243317 A1 | | 9/2002 | |
| GB | 1265770 A | | 3/1972 | |
| GB | 1535797 A | | 12/1978 | |
| JP | H0-2258 A | | 1/1990 | |
| JP | 2002-526513 A | | 8/2002 | |
| JP | 2003517027 A | | 5/2003 | |
| JP | 2014-531400 A | | 11/2014 | |
| JP | 2015-027963 A | | 2/2015 | |
| WO | 00/20360 A1 | | 4/2000 | |
| WO | 2013/016396 A2 | | 1/2013 | |
| WO | 2015/094697 A1 | | 6/2015 | |

OTHER PUBLICATIONS

International Search Report dated Feb. 24, 2018 in corresponding International Application No. PCT/CN2017/112812; 4 pages.
Chinese First Office Action dated Mar. 20, 2019 in corresponding Chinese Application No. 201710288532.3; 12 pages.
Chinese First Search Report dated Mar. 14, 2019 in corresponding Chinese Application No. 201710288532.3; 12 pages.
European Search Report dated Apr. 7, 2020, in corresponding European application No. 17907100.6; 9 pages.

* cited by examiner

FLUIDIZED BED REACTOR AND METHOD FOR PRODUCING PARA-XYLENE AND CO-PRODUCING LIGHT OLEFINS FROM BENZENE AND METHANOL AND/OR DIMETHYL ETHER

TECHNICAL FIELD

The present invention relates to a distributor in a fluidized bed, a reactor and a production method for producing para-xylene (PX) and co-producing light olefins, and is particularly suitable for a fluidized bed reactor and a production method for preparing para-xylene and co-producing light olefins by the alkylation of benzene and methanol, which belongs to the field of chemistry and chemical industry.

BACKGROUND

Para-xylene (PX) is one of the basic organic raw materials in the petrochemical industry, which has a wide range of applications in chemical fiber, synthetic resins, pesticides, pharmaceuticals and polymer materials. At present, the production of para-xylene mainly uses toluene, $C_9$ aromatics and mixed xylene as raw materials, and para-xylene is obtained by disproportionation, isomerization, adsorption separation or cryogenic separation. Since the para-xylene content in the product is controlled by thermodynamic equilibrium, para-xylene only accounts for ~24% of the $C_8$ mixed aromatics, and the material circulation processing amount is large during the process, and the equipment is large and the operation cost is high. In particular, the three isomers of xylene have small differences in boiling points, and it is difficult to obtain high-purity para-xylene by conventional distillation techniques, and an expensive adsorption separation process must be employed. In recent years, many patents at home and abroad have disclosed a new route for the production of para-xylene. The benzene-methanol alkylation technology is a new way to produce para-xylene with high selectivity, which has been highly valued and paid great attention by the industry.

Light olefins, namely ethylene and propylene, are two basic petrochemical feedstocks that are increasingly in demand Ethylene and propylene are mainly produced from naphtha, depending on the petroleum route. In recent years, the non-petroleum route to produce ethylene and propylene has received more and more attention, especially the process route of the methanol conversion to light olefins (MTO), which is an important way to achieve petroleum substitution strategy, reduce and alleviate our demand and dependence for petroleum.

The preparation of para-xylene by alkylation of toluene and methanol and the preparation of toluene and xylene by alkylation of benzene and methanol are new ways to increase the production of aromatics. The selective alkylation of toluene and methanol can produce highly selective para-xylene products, but the toluene required for this process is also an intermediate raw material for the production of para-xylene by an aromatics complex unit, which is in short supply in the market. While benzene is a by-product of the aromatics complex unit, it is estimated that an annual output of 800,000 tons of PX aromatics complex unit can produce about 300,000 tons of benzene. Therefore, the use of benzene as a raw material, alkylation with methanol to produce toluene and xylene will be an effective way to increase the production of aromatics.

A conventional toluene alkylation process involves mixing toluene and methanol upstream of the reactor and then feeding the mixture together into the reactor. The reactor type includes a fixed bed and a fluidized bed. In order to increase the conversion rate of toluene, the phased injection of reactants has been employed in various fixed bed and fluidized bed processes.

At present, most patent technologies related to benzene and methanol alkylation are aimed at increasing the yield of toluene and mixed xylene, but the yield of para-xylene is low.

The competition between the MTO reaction and the alkylation reaction is a major factor affecting the conversion rates of benzene and/or toluene, the yield of the para-xylene and the selectivity of light olefins. The process of preparing para-xylene and light olefins is acid-catalyzed reaction. Methanol-to-olefins reaction is inevitable in the process of preparing para-xylene by the alkylation of benzene and/or benzene and methanol based on the ZSM-5 molecular sieve catalyst. In the course of this reaction, the following reactions occur mainly:

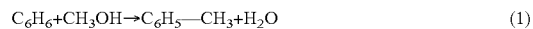

$$C_6H_6+CH_3OH \rightarrow C_6H_5\text{---}CH_3+H_2O \qquad (1)$$

$$C_6H_5\text{---}CH_3+CH_3OH \rightarrow C_6H_4\text{---}(CH_3)_2+H_2O \qquad (2)$$

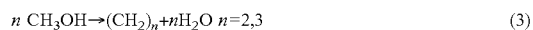

$$n\, CH_3OH \rightarrow (CH_2)_n + nH_2O \quad n=2,3 \qquad (3)$$

It can be seen from the above analysis that the technical field needs to coordinate and optimize the competition between the alkylation reaction and the MTO reaction from the two aspects of the catalyst design and the reactor design, so as to achieve synergistic effect and improve the conversion rate of toluene, the yield of para-xylene and the yield of light olefins.

SUMMARY

According to an aspect of the present application, this is provided a fluidized bed reactor for producing para-xylene and co-producing light olefins from benzene and methanol and/or dimethyl ether to achieve mass transfer control by distributing different raw materials stream in different regions in a co-feed system with a large difference in raw material reaction rates, so as to coordinate and optimize a co-feed system and improve the reaction yield. In the reaction of preparing para-xylene by the alkylation of benzene and methanol (including dimethyl ether), the reaction rates of the alkylation reaction and the MTO reaction are greatly different, and the MTO reaction rapidly consumes the alkylation reactant and inhibits the alkylation reaction. Therefore, the conversion rate of toluene is low. The fluidized bed reactor provided by the present application coordinates and optimizes the competition between the alkylation reaction and the MTO reaction by controlling the mass transfer process of methanol and benzene, so as to achieve synergism, thereby improving the conversion rate of benzene and the yield of para-xylene.

The fluidized bed reactor for producing para-xylene and co-producing light olefins from benzene and methanol and/or dimethyl ether, provided by the present application, comprising a first distributor and a second distributor, wherein the first distributor is located at the bottom of the fluidized bed, and the second distributor is located in at least one region of the gas flow downstream from the first distributor.

Methanol is both a raw material for the alkylation reaction of benzene and/or toluene and methanol, and a raw material for the MTO reaction, but the reaction rate of the MTO is much higher than that of the alkylation reaction of benzene and/or toluene and methanol. As our experimental studies show, when benzene and methanol are co-fed and the content of the methanol in the feedstock is low, the MTO reaction quickly consumes most of the methanol (alkylation reactant), inhibits the alkylation reaction of benzene and/or toluene and methanol, and the yield of toluene is low. When the content of methanol in the raw material is excessively excessive, the difference in the diffusion speed between methanol and benzene and/or toluene in the molecular sieve pores makes the adsorption amount of benzene and/or toluene per unit time low, which is also unfavorable for the alkylation reaction of benzene and/or toluene and methanol. Therefore, optimizing the concentrations of methanol and benzene and/or toluene in the reaction zone is an effective way to improve the conversion rate of benzene and the yield of para-xylene.

In the present application, light olefins include ethylene, propylene and butene.

In the present application, "methanol and/or dimethyl ether" means that methanol in the feedstock may be replaced in whole or in part by dimethyl ether, including three cases: only methanol; or only dimethyl ether; or both methanol and dimethyl ether. For example, "containing methanol and/or dimethyl ether and benzene" includes three cases: containing methanol and benzene; or containing dimethyl ether and benzene; or containing methanol, dimethyl ether and benzene. Unless otherwise specified, the methanol in the present application may be replaced by all or part of dimethyl ether and the amount of methanol may be calculated by converting dimethyl ether into methanol having the same number of carbon atoms.

Preferably, the second distributor comprises an intake pipe, a microporous pipe and an intake ring pipe;

the intake pipe is connected with a gas path of the microporous pipe, the gas is introduced by the intake pipe from the outside of the fluidized bed into the microporous pipe in the fluidized bed;

the intake ring pipe is connected with a gas path of the intake pipe, the intake ring pipe is disposed on a plane perpendicular to the flow direction of the gas from the first distributor;

the microporous pipe is disposed on the intake ring pipe and perpendicular to a plane of the intake ring pipe.

Preferably, material stream A enters the fluidized bed through the first distributor, material stream B enters the fluidized bed through the second distributor and contacts with at least a portion of the gas of the material stream A.

Preferably, the first distributor is a two-dimensional gas distributor and the first distributor distributes the gas on the plane in which the first distributor is located at the bottom of the fluidized bed.

Preferably, the second distributor is a three-dimensional gas distributor and the second distributor distributes the gas in at least a portion of the reaction space in which the second distributor is located in the fluidized bed.

In the present application, "at least a portion of the reaction space" refers to at least a portion of the space within the reaction zone.

Preferably, the first distributor is a branched pipe distributor and/or a plate distributor with blast caps.

Preferably, the second distributor is a microporous gas distributor.

Further preferably, the microporous pipe is a ceramic microporous pipe and/or a metal microporous sintered pipe.

Further preferably, the side and end faces of the microporous pipe have micropores with a pore diameter ranging from 0.5 µm to 50 µm.

Further preferably, the side and end faces of the microporous pipe have micropores with a porosity ranging from 25% to 50%.

Further preferably, the gas velocity in the pipe of the microporous pipe is in a range from 0.1 m/s to 10 m/s.

Still more preferably, the gas velocity in the pipe of the microporous pipe is in a range from 1 m/s to 10 m/s.

Still more preferably, the microporous pipes are arranged in plurality and arranged in parallel with each other; the intake ring pipes are arranged in plurality and arranged in a concentric ring or planar spiral in the same plane.

Preferably, the fluidized bed reactor comprises a reaction zone, a settling zone, a gas-solid separator, a stripping zone and a regenerated catalyst delivery pipe;

the first distributor is placed at the bottom of the reaction zone, the second distributor is placed above the first distributor, the settling zone is above the reaction zone, the settling zone is provided with the gas-solid separator, the stripping zone is below the reaction zone, and the regenerated catalyst delivery pipe is connected with the reaction zone.

As an embodiment, the regenerated catalyst delivery pipe is connected with the upper portion of the reaction zone.

As an embodiment, the regenerated catalyst delivery pipe is connected with the bottom of the reaction zone.

The inventors of the present application have found through research that, using benzene and methanol co-feeding, along the axial direction of the reactor, from upstream to downstream, the concentration of methanol decreases rapidly and approaches zero, while the concentration of benzene slowly decreases. In the upstream region of the reactor, the alkylation reaction rate is limited by the mass transfer rate of benzene in the catalyst pores, while in the downstream region of the reactor, with the rapid consumption of methanol and the rapid decrease of methanol diffusion, the alkylation reaction rate is limited by the mass transfer rate of methanol in the catalyst pores. In general, the conversion rate of benzene is low when the mixture is fed simultaneously. From the above analysis, maintaining a relatively stable concentration of methanol in the reactor is one of the effective ways to promote the alkylation reaction.

According to another aspect of the present application, this is provided a process for producing para-xylene and co-producing light olefins from benzene and methanol and/or dimethyl ether. By distributing different raw materials stream in different regions, to achieve mass transfer control, so as to coordinate and optimize a co-feed system and improve the reaction yield. The reaction of preparing para-xylene by the alkylation of benzene and methanol, in which the reaction rates of the alkylation reaction and the MTO reaction are greatly different, and the MTO reaction inhibits the alkylation reaction. Therefore, the conversion rate of benzene is low. The fluidized bed reactor provided by the present application coordinates and optimizes the competition between the alkylation reaction and the MTO reaction through mass transfer control, thereby improving the conversion rate of benzene and the yield of para-xylene.

The method for producing para-xylene and co-producing light olefins, provided by the present application, at least one of any of the above fluidized bed reactors are used; the method for producing para-xylene and co-producing light olefins comprises at least the following steps:

(1) passing the material stream A from the first distributor into the reaction zone of the fluidized bed reactor, the reaction zone containing a catalyst; the material stream A containing benzene, or the material stream A containing methanol and/or dimethyl ether and benzene;

(2) passing the material stream B containing methanol and/or dimethyl ether from the second distributor into the reaction zone of the fluidized bed reactor;

(3) in the reaction zone, contacting methanol and/or dimethyl ether and benzene from the material stream A and/or the material stream B, with the catalyst to form material stream C comprising para-xylene and light olefins.

Preferably, the method for producing para-xylene and co-producing light olefins further comprises the following steps:

(4) passing the material stream C into a settling zone and a gas-solid separator to separate the material stream C to obtain light olefins, para-xylene, chain hydrocarbon by-products, aromatic by-products and unconverted benzene, unconverted methanol and/or dimethyl ether;

(5) returning unconverted methanol and/or dimethyl ether to the fluidized bed reactor via the second distributor; returning the aromatic by-products and unconverted benzene to the fluidized bed reactor via the first distributor;

(6) forming a spent catalyst from the catalyst after carbon deposition in the reaction zone, the spent catalyst is then stripped in a stripper and regerated in a regenerator to obtain a regenerated catalyst; passing the regenerated catalyst into the fluidized bed reactor via the regenerated catalyst delivery pipe.

Wherein, the chain hydrocarbon by-product comprises at least one of methane, ethane, propane, butane and $C_{5+}$ chain hydrocarbon. The aromatic by-product comprises at least one of toluene, ethylbenzene, o-xylene, m-xylene and $C_{9+}$ arene.

In the present application, light olefins include at least one of ethylene, propylene and butene.

In the present application, "methanol and/or dimethyl ether" means that methanol in the feedstock may be replaced in whole or in part by dimethyl ether, including three cases: only methanol; or only dimethyl ether; or both methanol and dimethyl ether.

In the present application, "methanol and/or dimethyl ether and benzene" includes three cases: methanol and benzene; or dimethyl ether and benzene; or methanol, dimethyl ether and benzene.

Unless otherwise specified, the methanol in the present application may be replaced by all or part of dimethyl ether and the amount of methanol may be calculated by converting dimethyl ether into methanol having the same number of carbon atoms.

Preferably, the mass ratio of methanol in material stream B entering from the second distributor to methanol in material stream A entering from the first distributor is in a range from 1:1 to 20:1. The mass ratio of methanol here is compared by converting dimethyl ether (if contained) into methanol of the same number of carbon atoms.

Preferably, the sum of the mass percentages of methanol and dimethyl ether in material stream A is in a range from 0% to 30%. That is, the material stream A entering from the first distributor does not contain methanol, or the sum of the mass percentages of methanol in the material stream A entering from the first distributor does not exceed 30%.

Preferably, the sum of the mass percentages of methanol and dimethyl ether in material stream A is in a range from 2% to 20%.

Preferably, the fluidized bed reactor has a gas phase linear velocity ranging from 0.2 m/s to 2 m/s and a reaction temperature ranging from 300 C to 600° C.

Preferably, the regenerator has a gas phase linear velocity ranging from 0.2 m/s to 2 m/s and a regeneration temperature ranging from 500 C to 800° C.

The present application coordinates and optimizes the competition between the alkylation reaction and the MTO reaction by controlling the concentrations of methanol and/or dimethyl ether relative to benzene from the viewpoint of reactor design and process configuration, and improves the yield of para-xylene and the selectivity of light olefins to ensure that neither the situation of the inhibition of the alkylation reaction occurs due to the rapid consumption of most methanol and/or dimethyl ether by the MTO reaction, nor the situation against the alkylation reaction occurs due to far excess content of methanol and/or dimethyl ether, a large number of the MTO reaction occur, and lower adsorption amount of benzene in the catalyst per unit time.

The benefits brought out by the present application include:

(1) this is provided a fluidized bed reactor to achieve mass transfer control by distributing different raw materials stream in different regions in a co-feed system with a large difference in raw material reaction rates, so as to coordinate and optimize a co-feed system and improve the reaction yield.

(2) the fluidized bed reactor provided by the present application is applied to the reaction of producing para-xylene and co-producing light olefins from benzene and methanol and/or dimethyl ether, by distributing different raw materials stream in different regions and selective recycling, so as to improve the reaction yield.

(3) the method for producing para-xylene and co-producing light olefins from benzene and methanol and/or dimethyl ether, provided by the present application, has higher conversion rate of benzene and the selectivity of para-xylene, the conversion rate of benzene is more than 40%, the selectivity of para-xylene in the xylene isomer in the product is greater than 90%, the mass single-pass yield of para-xylene based on aromatics is greater than 25%, the conversion rate of methanol is greater than 90%, and the selectivity of (ethylene+propylene+butene) in $C_1$~$C_6$ chain hydrocarbon component is greater than 70%, and good technical results have been achieved.

Figure 1:
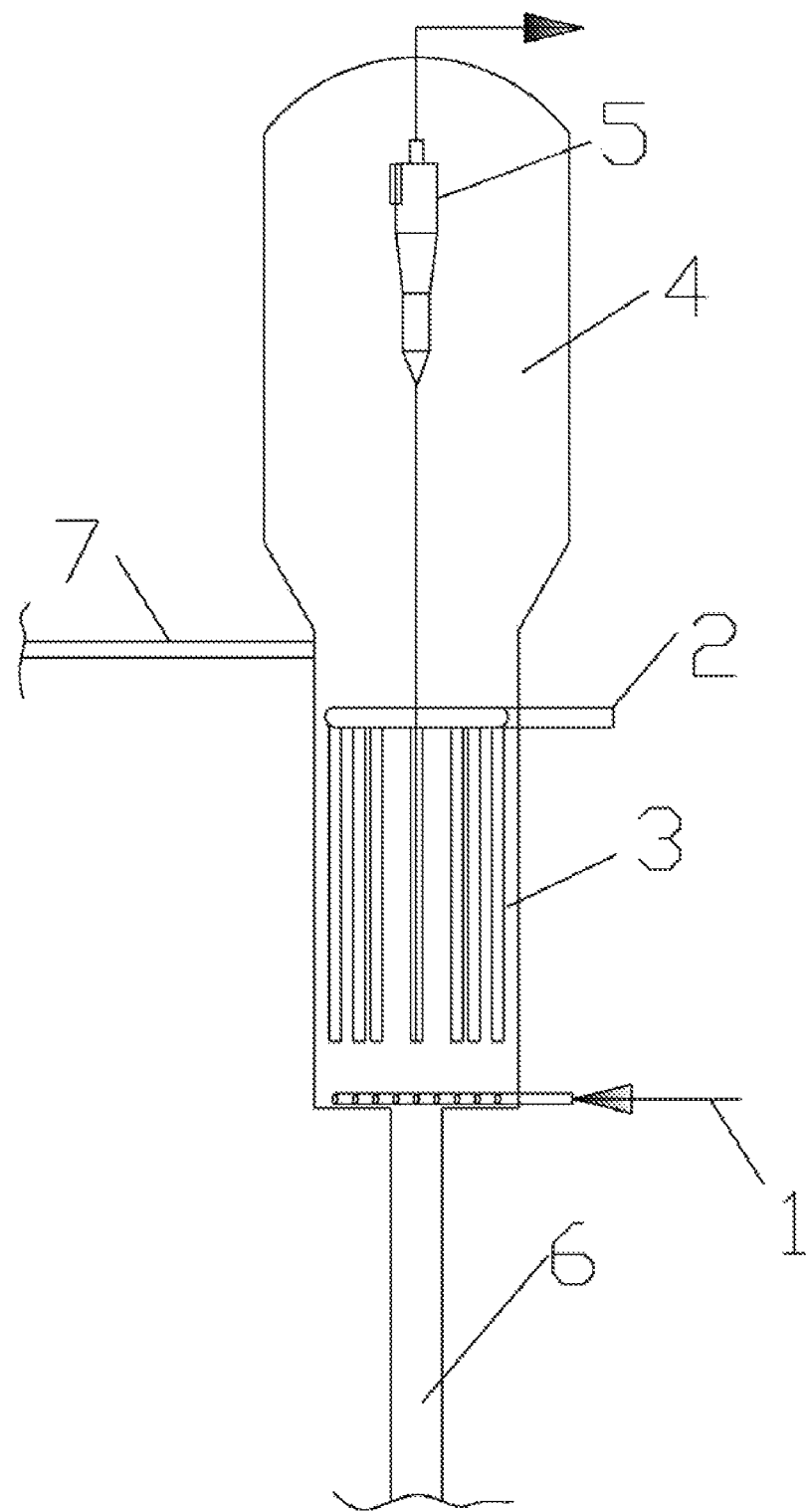
FIG. 1 is a schematic view of a fluidized bed reactor according to an embodiment of the present application.

The reference numerals in the figures are listed as follows:
1—first gas distributor, 2—second gas distributor, 3—reaction zone, 4—settling zone, 5—gas-solid separator, 6—stripping zone, 7—regenerated catalyst delivery pipe.
2-1—intake pipe, 2-2—intake ring pipe, 2-3—microporous pipe.

DETAILED DESCRIPTION OF THE EMBODIMENT

The present application will be described in detail below with reference to the embodiments, but the application is not limited to these embodiments.

Unless otherwise specified, the raw materials and catalysts in the embodiments of the present application are commercially available.

Figure 2:
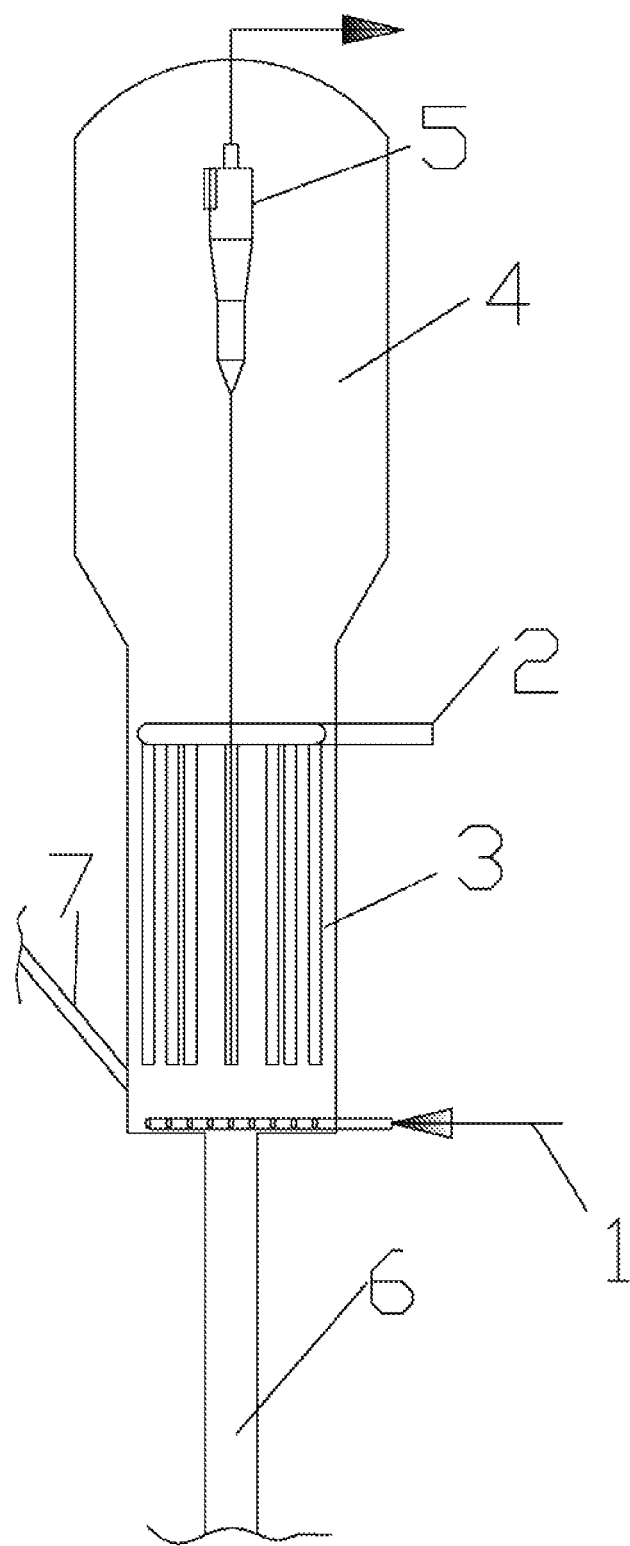
FIG. 2 is a schematic view of a fluidized bed reactor according to an embodiment of the present application.

According to one embodiment of the present application, a fluidized bed reactor for producing para-xylene and co-producing light olefins from benzene and methanol is shown in FIGS. 1 and 2, and comprises the first gas distributor 1, the second gas distributor 2, the reaction zone 3, the settling zone 4, the gas-solid separator 5, the stripping zone 6 and the regenerated catalyst delivery pipe 7.

The first gas distributor 1 is placed at the bottom of the reaction zone 3, the second gas distributor 2 is placed above the first gas distributor 1, the settling zone 4 is above the reaction zone 3, the gas-solid separator 5 is disposed within the settling zone 4, and the product outlet is set on the top. The stripping zone 6 is below the reaction zone 3, and the regenerated catalyst delivery pipe 7 is connected with the upper or bottom of the reaction zone 3. The regenerated catalyst enters the reaction zone from the regenerated catalyst delivery line 7 and the spent catalyst passes through the stripping zone 6 and enters the regenerator for regeneration.

As an embodiment of the present application, the first gas distributor 1 may be a branched pipe distributor.

As an embodiment of the present application, the first gas distributor 1 may be one of the plate distributor with blast caps.

As an embodiment of the present application, the second gas distributor 2 is a microporous gas distributor.

Figure 3:
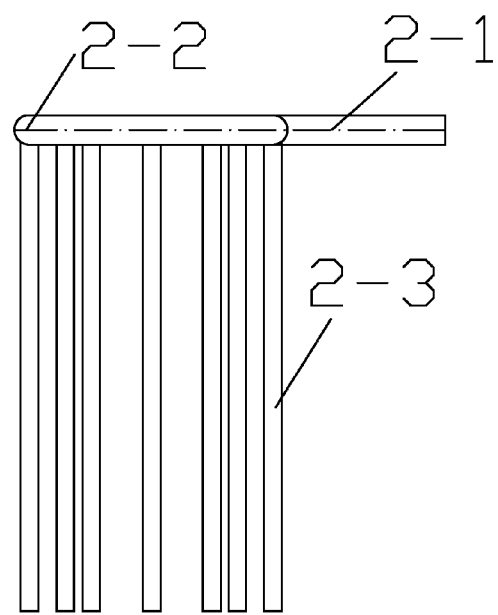
FIG. 3 is a side view of microporous gas distributor in the reaction zone according to an embodiment of the present application.

As an embodiment of the present application, as shown in FIG. 3, the microporous gas distributor includes the intake pipe 2-1, a plurality of intake ring pipes 2-2. The intake ring pipes 2-2 are centered on the axis of the reactor, and a plurality of microporous pipes 2-3 are uniformly distributed on the intake ring pipes 2-2. A plurality of microporous pipes 2-3 are uniformly distributed. The gas enters the microporous piped 2-3 through the intake pipe 2-1 and the intake ring pipe 2-2, and one end of the microporous pipe 2-3 is connected with the intake ring piped 2-2, and the other end is closed. The gas is discharged through the micropores in the microporous pipes 2-3.

The microporous pipe 2-3 can be a ceramic microporous pipe, a powder metallurgy microporous pipe, and the spacing between microporous pipes 2-3 is greater than 50 mm.

Figure 4:
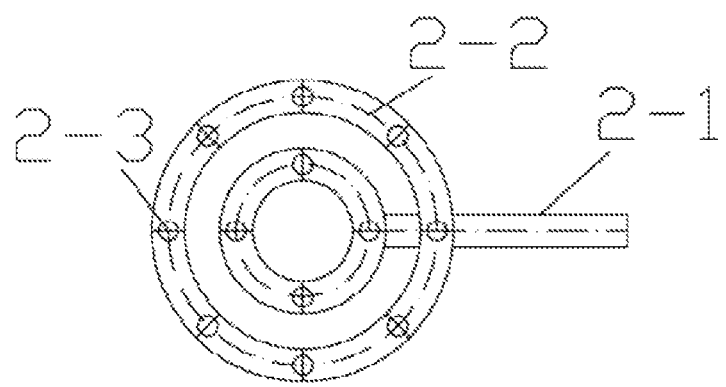
FIG. 4 is a top view of microporous gas distributor in the reaction zone according to an embodiment of the present application.

As shown in FIG. 3 and FIG. 4, in one embodiment of the present application, there are a total of 12 microporous pipes 2-3, all of which are arranged on the intake ring pipes 2-2 and perpendicular to the plane of the ring pipe, in a longitudinal parallel arrangement.

The side and end faces of the microporous pipes 2-3 have a uniform microporous structure, the pore diameter of the micropores is in a range from 0.5 µm to 50 µm, the porosity is in a range from 25% to 50%, and the gas velocity in the pipe is in a range from 0.1 to 10 m/s. Preferably, the gas velocity in the pipe is in a range from 1 m/s to 10 m/s.

As an embodiment of the present application, the microporous pipe 2-3 is placed in the reaction zone 3, which can inhibit the growth of bubbles, reduce the back mixing of gas, increase the exchange of substances between the dense phase and the dilute phase, and improve the reaction rate.

As an embodiment of the present application, the catalyst employed is a ZSM-5 molecular sieve catalyst.

Due to using benzene, methanol and/or dimethyl ether co-feeding, along the axial direction of the reactor, from upstream to downstream, the concentration of methanol and/or dimethyl ether decreases rapidly and approaches zero, while the concentration of benzene slowly decreases. In the upstream region of the reactor, the alkylation reaction rate is limited by the mass transfer rate of benzene in the catalyst pores, while in the downstream region of the reactor, with the rapid consumption of methanol and the rapid decrease of methanol diffusion, the alkylation reaction rate is limited by the mass transfer rate of methanol in the catalyst pores. Maintaining a relatively stable concentration of methanol in the reactor is one of the effective ways to promote the alkylation reaction.

As an embodiment of the present application, the first gas distributor 1 belongs to a two-dimensional gas distributor, that is, the raw gas is relatively uniformly distributed in the plane in which the first gas distributor 1 is located.

As an embodiment of the present application, the second gas distributor 2 (microporous gas distributor) belongs to a three-dimensional gas distributor, that is, the raw gas is relatively uniformly distributed in the three-dimensional space in which the second gas distributor 2 is located.

As an embodiment of the present application, benzene and aromatic by-products are introduced from the first gas distributor 1, and as the reaction proceeds, the concentration of benzene gradually decreases from upstream to downstream along the direction of the reactor axis.

As an embodiment of the present application, a portion of the methanol and/or dimethyl ether is introduced by the first gas distributor 1 and another portion of the methanol and/or dimethyl ether is introduced by the second gas distributor 2, which are distributed to the reaction zone 3 around the micropore core pipe 2-3 through the micropores densely arranged on microporous pipe 2-3. Therefore, in the region where the second gas distributor 2 is located, the concentration of methanol is substantially stabilized, and only in the downstream region of the reaction zone 3, the concentration of methanol rapidly decreases. The higher concentration of methanol in the region of the second gas distributor 2 can greatly improve the alkylation reaction rates of benzene and/or toluene.

As an embodiment of the present application, the method for producing para-xylene and co-producing light olefins comprises at least the following steps:

(1) passing the mixture of methanol and benzene from the first gas distributor into the reaction zone of the fluidized bed reactor;

(2) passing methanol from the second gas distributor into the reaction zone of the fluidized bed reactor, the mass ratio of the methanol entering from the second gas distributor to the methanol entering from the first gas distributor is in a range from 1:1 to 20:1;

(3) benzene and methanol in the reaction zone are contacted with the catalyst to form a gas phase stream comprising para-xylene and light olefins;

(4) passing the gas phase stream into a settling zone, a gas-solid separator, and entering a subsequent separation section via a product outlet, and after separation, to obtain ethylene, propylene, butene, para-xylene, dimethyl ether, chain hydrocarbon by-products, aromatic by-products and converted methanol and benzene, the chain hydrocarbon by-products include methane, ethane, propane, butane and $C_{5+}$ chain hydrocarbons, and the aromatic by-products include benzene, ethylbenzene, o-xylene, m-xylene and $C_{9+}$ aromatic hydrocarbons;

(5) returning dimethyl ether and unconverted methanol as raw material to the fluidized bed reactor via the second gas distributor to recycle, and returning the aromatic by-products and unconverted benzene as raw material to the fluidized bed reactor via the first gas distributor to recycle;

(6) forming a spent catalyst from the catalyst after carbon deposition in the reaction zone, the spent catalyst is then stripped in a stripper and regerated in a fluidized bed regenerator, and passing the regenerated catalyst into the fluidized bed reactor via the regenerated catalyst delivery pipe.

In the above method, the fluidized bed reactor has a gas phase linear velocity ranging from 0.2 m/s to 2 m/s and a temperature ranging from 300° C. to 600° C., and the fluidized bed regenerator has a gas phase linear velocity ranging from 0.2 m/s to 2 m/s and a temperature ranging from 500° C. to 800° C.

Example 1

In the fluidized bed reactor as shown in FIG. 1, para-xylene and light olefins are produced. The fluidized bed reactor comprises the first gas distributor 1, the second gas distributor 2, the reaction zone 3, the settling zone 4, the gas-solid separator 5, the stripping zone 6 and the regenerated catalyst delivery pipe 7. The first gas distributor 1 is placed at the bottom of the reaction zone 3. The second gas distributor 2 is placed in the reaction zone 3. The settling zone 4 is above the reaction zone 3. The gas-solid separator 5 is disposed within the settling zone 4, and the product outlet is set on the top. The stripping zone 6 is below the reaction zone 3, and the upper portion of the reaction zone 3 is connected with the regenerated catalyst delivery pipe 7.

The first gas distributor 1 is a branched pipe distributor, and the second gas distributor 2 is a microporous gas distributor.

As shown in FIG. 3, the microporous gas distributor includes the intake pipe 2-1, the intake ring pipe 2-2 and the microporous pipe 2-3. As shown in FIG. 4, the intake pipe 2-1 is connected to two intake ring pipes 2-2, the intake ring pipes 2-2 are uniformly provided with twelve microporous pipes 2-3. The microporous pipes 2-3 is a powder metallurgy microporous pipe, and the spacing between microporous pipes 2-3 is 150 mm, the pore diameter of the micropores is 1 μm, the porosity is 35%, and the gas velocity in the pipe is 5 m/s.

The catalyst in the fluidized bed reactor is a ZSM-5 molecular sieve catalyst.

Material Stream A: the mixture of benzene, aromatic by-products and methanol. Material stream A enters the reaction zone 3 of the fluidized bed reactor via the first gas distributor 1, and the mass content of methanol in the mixture of material stream A is 4%.

Material Stream B: methanol. The material stream B enters the reaction zone 3 of the fluidized bed reactor from the second gas distributor 2, and the mass ratio of the methanol entering from the second gas distributor 2 to the methanol entering from the first gas distributor 1 is 9:1. The fluidized bed reactor has a gas phase linear velocity ranging from 0.8 m/s to 1.0 m/s and a temperature of 450° C. The reactants in the reaction zone 3 are contacted with the catalyst to form a gas phase stream comprising para-xylene and light olefins. The gas phase stream enters the settling zone 4, the gas-solid separator 5, and enters a subsequent separation section via the product outlet. The catalyst forms the spent catalyst after carbon deposition in the reaction zone, and the spent catalyst is fed into the fluidized bed regenerator for regeneration. The gas phase linear velocity of the fluidized bed regenerator is 1.0 m/s and the temperature is 650° C. The regenerated catalyst enters the fluidized bed reactor via the regenerated catalyst delivery pipe 7.

The product composition is analyzed by gas chromatography. The results show that the conversion rate of benzene is 41%, the conversion rate of methanol is 99%, and the mass single-pass yield of para-xylene based on aromatics is 26%, the selectivity of para-xylene in the xylene isomer in the products is 99%, and the selectivity of light olefins (ethylene+propylene+butene) in $C_1$~$C_6$ chain hydrocarbon component is 75%.

Example 2

In the fluidized bed reactor as shown in FIG. 1, para-xylene and light olefins are produced. The fluidized bed reactor comprises the first gas distributor 1, the second gas distributor 2, the reaction zone 3, the settling zone 4, the gas-solid separator 5, the stripping zone 6 and the regenerated catalyst delivery pipe 7. The first gas distributor 1 is placed at the bottom of the reaction zone 3. The second gas distributor 2 is placed in the reaction zone 3. The settling zone 4 is above the reaction zone 3. The gas-solid separator 5 is disposed within the settling zone 4, and the product outlet is set on the top. The stripping zone 6 is below the reaction zone 3, and the upper portion of the reaction zone 3 is connected with the regenerated catalyst delivery pipe 7.

The first gas distributor 1 is a branched pipe distributor, and the second gas distributor 2 is a microporous gas distributor.

As shown in FIG. 3, the microporous gas distributor includes the intake pipe 2-1, the intake ring pipe 2-2 and the microporous pipe 2-3. As shown in FIG. 4, the intake pipe 2-1 is connected to two intake ring pipes 2-2, the intake ring pipes 2-2 are uniformly to provided with twelve microporous pipes 2-3. The microporous pipes 2-3 is a ceramic microporous pipe, and the spacing between microporous pipes 2-3 is in a range from 150 mm to 200 mm, the pore diameter of the micropores is in a range from 20 μm to 40 μm, the porosity is 45%, and the gas velocity in the pipe is 4 m/s.

The catalyst in the fluidized bed reactor is a ZSM-5 molecular sieve catalyst.

Material Stream A: the mixture of benzene, aromatic by-products and dimethyl ether. Material stream A enters the reaction zone 3 of the fluidized bed reactor via the first gas distributor 1, and the mass content of dimethyl ether in the mixture of material stream A is 10%.

Material Stream B: methanol. The material stream B enters the reaction zone 3 of the fluidized bed reactor from the second gas distributor 2, and the mass ratio of the methanol entering from the second gas distributor 2 to the methanol entering from the first gas distributor 1 is 19:1. The fluidized bed reactor has a gas phase linear velocity ranging from 1.3 m/s to 1.5 m/s and a temperature of 500° C. The reactants in the reaction zone 3 are contacted with the catalyst to form a gas phase stream comprising para-xylene and light olefins. The gas phase stream enters the settling zone 4, the gas-solid separator 5, and enters a subsequent separation section via the product outlet. The catalyst forms the spent catalyst after carbon deposition in the reaction zone, and the spent catalyst is fed into the fluidized bed regenerator for regeneration. The gas phase linear velocity of the fluidized bed regenerator is 1.0 m/s and the temperature is 600° C. The regenerated catalyst enters the fluidized bed reactor via the regenerated catalyst delivery pipe 7.

The product composition is analyzed by gas chromatography. The results show that the conversion rate of benzene is 45%, the conversion rate of methanol is 91%, and the mass single-pass yield of para-xylene based on aromatics is 37%, the selectivity of para-xylene in the xylene isomer in the products is 92%, and the selectivity of light olefins (ethylene+propylene+butene) in $C_1$~$C_6$ chain hydrocarbon component is 71%.

Example 3

In the fluidized bed reactor as shown in FIG. 1, para-xylene and light olefins are produced. The fluidized bed reactor comprises the first gas distributor 1, the second gas distributor 2, the reaction zone 3, the settling zone 4, the gas-solid separator 5, the stripping zone 6 and the regenerated catalyst delivery pipe 7. The first gas distributor 1 is placed at the bottom of the reaction zone 3. The second gas distributor 2 is placed in the reaction zone 3. The settling zone 4 is above the reaction zone 3. The gas-solid separator 5 is disposed within the settling zone 4, and the product outlet is set on the top. The stripping zone 6 is below the reaction zone 3, and the upper portion of the reaction zone 3 is connected with the regenerated catalyst delivery pipe 7.

The first gas distributor 1 is a plate distributor with blast caps, and the second gas distributor 2 is a microporous gas distributor.

As shown in FIG. 3, the microporous gas distributor includes the intake pipe 2-1, the intake ring pipe 2-2 and the microporous pipe 2-3. As shown in FIG. 4, the intake pipe 2-1 is connected to two intake ring pipes 2-2, the intake ring pipes 2-2 are uniformly provided with twelve microporous pipes 2-3. The microporous pipes 2-3 is a ceramic microporous pipe, and the spacing between microporous pipes 2-3 is in a range from 100 mm to 150 mm, the pore diameter of the micropores is in a range from 5 μm to 20 μm, the porosity is 45%, and the gas velocity in the pipe is 8 m/s.

The catalyst in the fluidized bed reactor is a ZSM-5 molecular sieve catalyst.

Material Stream A: the mixture of benzene, aromatic by-products, methanol and dimethyl ether. Material stream A enters the reaction zone 3 of the fluidized bed reactor via the first gas distributor 1, and the mass content of methanol (calculated by converting dimethyl ether to methanol with the same number of carbon atoms) in the mixture of material stream A is 8%.

Material Stream B: methanol and dimethyl ether. The material stream B enters the reaction zone 3 of the fluidized bed reactor from the second gas distributor 2, and the mass ratio of the methanol entering from the second gas distributor 2 to the methanol entering from the first gas distributor 1 is 9:1. The fluidized bed reactor has a gas phase linear velocity ranging from 0.2 to 0.3 m/s and a temperature of 550° C. The reactants in the reaction zone 3 are contacted with the catalyst to form a gas phase stream C comprising para-xylene and light olefins. The gas phase stream enters the settling zone 4, the gas-solid separator 5, and enters a subsequent separation section via the product outlet. The catalyst forms the spent catalyst after carbon deposition in the reaction zone, and the spent catalyst is fed into the fluidized bed regenerator for regeneration. The gas phase linear velocity of the fluidized bed regenerator is 1.0 m/s and the temperature is 700° C. The regenerated catalyst enters the fluidized bed reactor via the regenerated catalyst delivery pipe 7.

The product composition is analyzed by gas chromatography. The results show that the conversion rate of dimethyl ether is 42%, the conversion rate of methanol is 94%, to and the mass single-pass yield of para-xylene based on aromatics is 29%, the selectivity of para-xylene in the xylene isomer in the products is 95%, and the selectivity of light olefins (ethylene+propylene+butene) in $C_1$~$C_6$ chain hydrocarbon component is 74%.

Example 4

In the fluidized bed reactor as shown in FIG. 2, para-xylene and light olefins are produced. The fluidized bed reactor comprises the first gas distributor 1, the second gas distributor 2, the reaction zone 3, the settling zone 4, the gas-solid separator 5, the stripping zone 6 and the regenerated catalyst delivery pipe 7. The first gas distributor 1 is placed at the bottom of the reaction zone 3. The second gas distributor 2 is placed in the reaction zone 3. The settling zone 4 is above the reaction zone 3. The gas-solid separator 5 is disposed within the settling zone 4, and the product outlet is set on the top. The stripping zone 6 is below the reaction zone 3, and the upper portion of the reaction zone 3 is connected with the regenerated catalyst delivery pipe 7.

The first gas distributor 1 is a branched pipe distributor, and the second gas distributor 2 is a microporous gas distributor.

As shown in FIG. 3, the microporous gas distributor includes the intake pipe 2-1, the intake ring pipe 2-2 and the microporous pipe 2-3. As shown in FIG. 4, the intake pipe 2-1 is connected to two intake ring pipes 2-2, the intake ring pipes 2-2 are uniformly provided with twelve microporous pipes 2-3. The microporous pipes 2-3 is a ceramic microporous pipe, and the spacing between microporous pipes is in a range from 150 mm to 200 mm, the pore diameter of the micropores is in a range from 5 μm to 20 μm, the porosity is 40%, and the gas velocity in the pipe is 6 m/s.

The catalyst in the fluidized bed reactor is a ZSM-5 molecular sieve catalyst.

Material Stream A: the mixture of benzene, aromatic by-products and methanol. Material stream A enters the reaction zone 3 of the fluidized bed reactor via the first gas distributor 1, and the mass content of methanol in the mixture of material stream A is 20%.

Material Stream B: methanol. The material stream B enters the reaction zone 3 of the fluidized bed reactor from the second gas distributor 2, and the mass ratio of the methanol entering from the second gas distributor 2 to the methanol entering from the first gas distributor 1 is 5:1. The fluidized bed reactor has a gas phase linear velocity ranging from 1.5 m/s to 1.7 m/s and a temperature of 530° C. The reactants in the reaction zone 3 are contacted with the catalyst to form a gas phase stream comprising para-xylene and light olefins. The gas phase stream enters the settling zone 4, the gas-solid separator 5, and enters a subsequent separation section via the product outlet. The catalyst forms the spent catalyst after carbon deposition in the reaction zone, and the spent catalyst is fed into the fluidized bed regenerator for regeneration. The gas phase linear velocity of the fluidized bed regenerator is 2.0 m/s and the temperature is 700° C. The regenerated catalyst enters the fluidized bed reactor via the regenerated catalyst delivery pipe 7.

The product composition is analyzed by gas chromatography. The results show that the conversion rate of benzene is 49%, the conversion rate of methanol is 92%, and the mass single-pass yield of para-xylene based on aromatics is 32%, the selectivity of para-xylene in the xylene isomer in the products is 93%, and the selectivity of light olefins (ethylene+propylene+butene) in $C_1$~$C_6$ chain hydrocarbon component is 73%.

The above description is only a few embodiments of the present application, and is not intended to limit the application in any way. While the present application has been described above with reference to preferred embodiments, but these embodiments are not intended to limit the present application. Without departing from the spirit of the present application, one skilled in the art will be able to make several possible variations and modifications and thus the protection scope shall be determined by the scope as defined in the claims.

What is claimed is:

1. A fluidized bed reactor for producing para-xylene and co-producing light olefins from benzene and methanol and/or dimethyl ether, comprising a reaction zone, a first distributor, and a second distributor, wherein the first distributor is located at the bottom of the reaction zone of a fluidized bed, and the second distributor is placed above the first distributor, wherein the second distributor comprises an intake pipe, a plurality of microporous pipes and a plurality of intake ring pipes, the intake pipe is connected with a gas path of the microporous pipes, gas is introduced by the intake pipes from the outside of the fluidized bed into the microporous pipes in the fluidized bed;

the intake ring pipes are connected with a gas path of the intake pipe, the intake ring pipes are disposed on a plane perpendicular to the flow direction of the gas from the first distributor;

the microporous pipes are disposed on the intake ring pipes and perpendicular to a plane of the intake ring pipes, wherein, side and end faces of the microporous pipes have a uniform microporous structure such that the gas is uniformly distributed in the three-dimensional space in which the second distributor is located; and wherein, the fluidized bed reactor further comprises a regenerated catalyst delivery pipe which is connected with the bottom of the reaction zone.

2. The fluidized bed reactor of claim 1, wherein the first distributor is a two-dimensional gas distributor and the first distributor distributes the gas on the plane in which the first distributor is located at the bottom of the reaction zone of the fluidized bed.

3. The fluidized bed reactor of claim 1, wherein the first distributor is a branched pipe distributor or a plate distributor with blast caps.

4. The fluidized bed reactor of claim 1, wherein the microporous pipes are ceramic microporous pipes or powder metallurgical microporous pipes.

5. The fluidized bed reactor of claim 1, wherein side and end faces of the microporous pipes have micropores with a pore diameter ranging from 0.5 µm to 50 µm and a porosity ranging from 25% to 50%.

6. The fluidized bed reactor of claim 1, wherein the microporous pipes are arranged in parallel with each other; the intake ring pipes are arranged in a concentric ring or planar spiral in the same plane.

7. The fluidized bed reactor of claim 1, wherein the fluidized bed reactor comprises a settling zone, a gas-solid separator, and a stripping zone;

the settling zone is above the reaction zone, the settling zone is provided with the gas-solid separator, the stripping zone is below the reaction zone.

8. A method for producing para-xylene and co-producing light olefins from benzene and methanol and/or dimethyl ether, wherein a fluidized bed reactors comprising a reaction zone, a first distributor and a second distributor is used, wherein the first distributor is located at the bottom of the reaction zone of a fluidized bed, and the second distributor is placed above the first distributor;

wherein the second distributor comprises an intake pipe, a plurality of microporous pipes and a plurality of intake ring pipes, the intake pipe is connected with a gas path of the microporous pipes, the gas is introduced by the intake pipe from the outside of the fluidized bed into the microporous pipes in the fluidized bed;

the intake ring pipes are connected with a gas path of the intake pipe, the intake ring pipes are disposed on a plane perpendicular to the flow direction of the gas from the first distributor;

the microporous pipes are disposed on the intake ring pipes and perpendicular to a plane of the intake ring pipes, wherein, side and end faces of the microporous pipes have a uniform microporous structure such that gas is uniformly distributed in the three-dimensional space in which the second gas distributor is located;

wherein, the fluidized bed reactor further comprises a regenerated catalyst delivery pipe which is connected with the bottom of the reaction zone, the method comprising:

(1) passing a material stream A from the first distributor into the reaction zone of the fluidized bed reactor, the reaction zone containing a catalyst; the material stream A containing benzene, or the material stream A containing methanol and/or dimethyl ether and benzene;

(2) passing a material stream B containing methanol and/or dimethyl ether from the second distributor into the reaction zone of the fluidized bed reactor; and (3) in the reaction zone, contacting methanol and/or dimethyl ether and benzene from the material stream A and/or the material stream B, with the catalyst to form material stream C comprising para-xylene and light olefins.

9. The method of claim 8, wherein the method for producing para-xylene and co-producing light olefins from methanol and/or dimethyl ether and benzene further comprises the following steps:

(4) passing the material stream C into a settling zone and a gas-solid separator to separate the material stream C to obtain light olefins, para-xylene, chain hydrocarbon by-products, aromatic by-products and unconverted benzene, unconverted methanol and/or dimethyl ether;

(5) returning unconverted methanol and/or dimethyl ether to the fluidized bed reactor via the second distributor; returning the aromatic by-products and unconverted benzene to the fluidized bed reactor via the first distributor; and (6) forming a spent catalyst from the catalyst after carbon deposition in the reaction zone, the spent catalyst is then stripped in a stripper and regenerated in a regenerator to obtain a regenerated catalyst; passing the regenerated catalyst into the fluidized bed reactor via the regenerated catalyst delivery pipe.

10. The method of claim 8, wherein the mass ratio of methanol and/or dimethyl ether in material stream B to methanol and/or dimethyl ether in material stream A is in a range from 1:1 to 20:1.

11. The method of claim 8, wherein, the material stream A contains benzene, but the material stream A entering from the first distributor does not contain methanol.

12. The method of claim 8, wherein the material stream A contains methanol and dimethyl ether and benzene, and the sum of the mass percentages of methanol and dimethyl ether in material stream A entering from the first distributor is in a range from 2% to 20%.

13. The method of claim 8, wherein the fluidized bed reactor has a gas phase linear velocity ranging from 0.2 m/s to 2 m/s and a reaction temperature ranging from 300° C. to 600° C.

14. The method of claim 9, wherein the regenerator has a gas phase linear velocity ranging from 0.2 m/s to 2 m/s and a regeneration temperature ranging from 500° C. to 800° C.

* * * * *